(12) United States Patent
Knapp et al.

(10) Patent No.: US 11,315,674 B2
(45) Date of Patent: Apr. 26, 2022

(54) SYSTEMS AND METHODS FOR MEDICINE DELIVERY

(71) Applicant: Becton, Dickinson and Company, Franklin Lakes, NJ (US)

(72) Inventors: Keith Knapp, Warwick, NY (US); Neil McCaffrey, Mill Valley, CA (US); Jay Butterbrodt, North Andover, MA (US); Margaret Taylor, Groton, MA (US); Ruth Markowitz, Franklin Lakes, NJ (US); Gary Searle, Norfolk, MA (US); Michael Gibney, Chestnut Ridge, NY (US); James Salemme, Billerica, MA (US); James Walker, Franklin Lakes, NJ (US); Sean Sullivan, Ridgewood, NJ (US); Ernest Elgin, Franklin Lakes, NJ (US); Rita Saltiel-Berzin, Franklin Lakes, NJ (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 59 days.

(21) Appl. No.: 15/519,402

(22) PCT Filed: Oct. 20, 2015

(86) PCT No.: PCT/US2015/056517
§ 371 (c)(1),
(2) Date: Apr. 14, 2017

(87) PCT Pub. No.: WO2016/064916
PCT Pub. Date: Apr. 28, 2016

(65) Prior Publication Data
US 2017/0232204 A1 Aug. 17, 2017

Related U.S. Application Data

(60) Provisional application No. 62/066,351, filed on Oct. 20, 2014.

(51) Int. Cl.
*A61M 5/31* (2006.01)
*G16H 20/60* (2018.01)
(Continued)

(52) U.S. Cl.
CPC ............. *G16H 20/60* (2018.01); *A47G 21/00* (2013.01); *A61J 7/0436* (2015.05); *A61J 7/0481* (2013.01);
(Continued)

(58) Field of Classification Search
CPC .................. A61M 5/31568; A61M 5/3157
See application file for complete search history.

(56) References Cited

U.S. PATENT DOCUMENTS 2,956,563 A * 10/1960 Sarnoff ................... A61M 5/28
604/232
5,176,640 A 1/1993 Nacci et al.
(Continued)

FOREIGN PATENT DOCUMENTS

CA 2874331 A1 11/2013
EP 2730306 A1 5/2004
(Continued)

*Primary Examiner* — Nathan R Price
*Assistant Examiner* — Courtney B Fredrickson
(74) *Attorney, Agent, or Firm* — Dickinson Wright, PLLC

(57) ABSTRACT

Improved systems and methods for medicine delivery, and in particular, improved insulin pen needles and related devices are provided. Smart injection devices record and transfer data including medicine level, delivered dose, dose confirmation, and dose time and date. Additional data captured may include glucose concentration, insulin level, carbohydrates ingested, stress level, exercise, blood pressure, and glucose high and low excursion events. Various means of data collection and analysis are provided and systems can identify and flag patients who require intervention. Smart sleeves and add sensing capability to standard insulin pens.

(Continued)

Pen needles are provided with sensing capability to confirm and measure doses delivered by insulin pen. A two-part pen cap include a primary sleeve that connects to the insulin pen and an end cap that provides for capturing the time of dose delivery, and monitoring the hold time for a dose delivery after plunger movement.

3 Claims, 15 Drawing Sheets

(51) Int. Cl.

| | | |
|---|---|---|
| *A61M 5/32* | (2006.01) | |
| *A47G 21/00* | (2006.01) | |
| *A61J 7/04* | (2006.01) | |
| *A61M 5/28* | (2006.01) | |
| *A61M 5/34* | (2006.01) | |
| *A61M 5/24* | (2006.01) | |
| *G16H 20/17* | (2018.01) | |
| *A61M 5/315* | (2006.01) | |
| *G09B 19/00* | (2006.01) | |
| *G01F 13/00* | (2006.01) | |
| *A61M 5/20* | (2006.01) | |
| *A61M 39/02* | (2006.01) | |
| *A61J 1/14* | (2006.01) | |
| *A61M 5/42* | (2006.01) | |

(52) U.S. Cl.
CPC ............ *A61M 5/2422* (2013.01); *A61M 5/28* (2013.01); *A61M 5/281* (2013.01); *A61M 5/31568* (2013.01); *A61M 5/3202* (2013.01); *A61M 5/3204* (2013.01); *A61M 5/3278* (2013.01); *A61M 5/34* (2013.01); *A61M 5/347* (2013.01); *G09B 19/00* (2013.01); *G16H 20/17* (2018.01); *A61J 1/1412* (2013.01); *A61J 2200/30* (2013.01); *A61J 2200/70* (2013.01); *A61J 2200/74* (2013.01); *A61M 5/31525* (2013.01); *A61M 5/427* (2013.01); *A61M 2005/2073* (2013.01); *A61M 2005/3258* (2013.01); *A61M 2005/3267* (2013.01); *A61M 2005/3284* (2013.01); *A61M 2039/0267* (2013.01); *A61M 2205/13* (2013.01); *A61M 2205/15* (2013.01); *A61M 2205/18* (2013.01); *A61M 2205/3306* (2013.01); *A61M 2205/3317* (2013.01); *A61M 2205/3344* (2013.01); *A61M 2205/3375* (2013.01); *A61M 2205/3379* (2013.01); *A61M 2205/3553* (2013.01); *A61M 2205/3592* (2013.01); *A61M 2205/50* (2013.01); *A61M 2205/52* (2013.01); *A61M 2205/6027* (2013.01); *A61M 2205/6045* (2013.01); *A61M 2205/6054* (2013.01); *A61M 2205/80* (2013.01); *A61M 2230/50* (2013.01); *A61M 2230/63* (2013.01); *G01F 13/00* (2013.01)

(56) References Cited

U.S. PATENT DOCUMENTS

| | | | |
|---|---|---|---|
| 5,593,390 A * | 1/1997 | Castellano | A61M 5/2455 604/208 |
| 6,620,133 B1 * | 9/2003 | Steck | A61M 5/20 604/131 |
| 9,999,718 B2 * | 6/2018 | Brady | A61M 5/31568 |
| 2004/0073196 A1 | 4/2004 | Adams et al. | |
| 2005/0182358 A1 * | 8/2005 | Veit | A61B 5/14532 604/93.01 |
| 2008/0108951 A1 | 5/2008 | Jerde et al. | |
| 2008/0154202 A1 * | 6/2008 | Nemoto | A61M 5/14546 604/154 |
| 2009/0177068 A1 | 7/2009 | Stivoric et al. | |
| 2009/0299279 A1 | 12/2009 | Richter | |
| 2010/0049126 A1 * | 2/2010 | Bronfeld | A61B 5/150114 604/113 |
| 2012/0292219 A1 | 11/2012 | Terwilliger et al. | |
| 2013/0310756 A1 * | 11/2013 | Whalley | A61M 5/31 604/189 |
| 2014/0213985 A1 * | 7/2014 | Teucher | A61M 5/2455 604/208 |
| 2014/0288422 A1 | 9/2014 | Brady et al. | |
| 2016/0074587 A1 * | 3/2016 | Searle | A61M 5/16804 604/189 |

FOREIGN PATENT DOCUMENTS

| | | |
|---|---|---|
| GB | 2406520 A | 4/2005 |
| JP | 2014528783 A | 10/2014 |
| WO | WO-2014075685 A2 | 5/2014 |
| WO | 2014136462 A1 | 9/2014 |

\* cited by examiner

SYSTEMS AND METHODS FOR MEDICINE DELIVERY

CROSS REFERENCE TO RELATED APPLICATIONS

This application claims the benefit of U.S. provisional patent application No. 62/066,351 filed Oct. 20, 2014, the entire contents of which are hereby incorporated by reference.

FIELD OF THE INVENTION

The present invention relates to improved systems and methods for medicine delivery. In particular, the present invention relates to improved insulin pen needles and related devices.

BACKGROUND OF THE INVENTION

Related information may be found in U.S. Published Application No. 2014/0188074, U.S. Pat. Nos. 8,613,719 and 8,817,258, U.S. Patent Application Nos. 61/898,936, filed Nov. 1, 2013, 62/032,318, filed Aug. 1, 2014, Ser. No. 14/485,749, filed Sep. 14, 2014, 61/911,850, filed Dec. 4, 2013, and International Patent Application No. WO 2013/177135, the entire contents of each of which are hereby incorporated by reference.

Diabetes is a group of diseases marked by high levels of blood glucose resulting from defects in insulin production, insulin action, or both. There are 25.8 million people in the United States, or 8.3% of the population, who have diabetes. The total prevalence of diabetes has increased 13.5% since the 2005-2007 time period. Diabetes can lead to serious complications and premature death, but there are well-known products available for people with diabetes to help control the disease and lower the risk of complications. Chronic hyperglycemia leads to serious sometimes irreversible complications including renal failure, peripheral neuropathy, retinopathy, and vascular system complications.

Treatment options for people with diabetes include specialized diets, oral medications and/or insulin therapy. The primary goal for diabetes treatment is to control the patient's blood glucose (sugar) level in order to increase the chances of a complication-free life.

Idealized diabetes therapy would include continuous monitoring of blood glucose levels, data capture for insulin dosing, dietary intake, such as carbohydrate estimation, activity tracking, stress levels, and other factors. By continuously monitoring, healthcare professionals can maximize the effectiveness of the treatment regimen for each patient. Unfortunately, conventional diabetes treatments, including multiple daily injections (MDI), insulin pens, patch pumps and insulin pumps, do not adequately record information on medication doses delivered to the patient to provide feedback to the doctor. Accordingly, the conventional feedback loop between doctors and patients is less frequent, and based mainly on qualitative assessments between the doctor and patient. Accordingly, there is a need to enhance medication delivery devices and methods to add informatics such as dose delivery capture, to provide enhanced feedback to healthcare professionals to improve diabetes therapy.

In order to properly diagnose and treat diabetes mellitus (DM) the patient and/or Health Care Provider (HCP) needs to evaluate the short-term, daily records for (1) insulin dosing, (2) oral medications, (3) Blood Glucose Measurement (BGM), and (4) carbohydrate intake. These data are obtained from different sources, such as the setting on an insulin pen, the episodic reading from a BGM meter, and the estimate of carbohydrates in a meal all determined and transposed by the patient into a logbook or diary. This method of recording data is extremely tedious and prone to errors and omissions. Even in the best case scenario, when the historical records are complete, the insight that can be obtained is limited without transposing the hand written data to software that can reconfigure the data to evaluate trends and support therapeutic modifications. As a result the majority of patients do not properly maintain their logbook, which reduces the ability of the patient and the doctor to properly diagnose the disease, which can ultimately result in poor adherence to therapy and poor glycemic control. Accordingly, a system is required to automatically capture, store, transfer, and enable optimal assessment of all the data necessary for the proper diagnosis and treatment of Diabetes Mellitus.

U.S. Pat. No. 8,613,719 describes a monitor that can be attached to the patch pen, which can sense and wirelessly transmit the time of each delivery event. A flag, such as a magnet, is placed on the movable linkage within the patch pen, and a sensor within the monitor attachment detects the proximity of the magnet at the end of the linkage travel, that is, at the end of the delivery cycle.

Related concepts are described in U.S. Patent Application Nos. 61/898,936, filed Nov. 1, 2013, 62/032,318, filed Aug. 1, 2014 and Ser. No. 14/485,749, filed Sep. 14, 2014, the entire contents of each of which are hereby incorporated by reference.

SUMMARY OF THE INVENTION

Patients may not realize they are noncompliant to therapeutic recommendations or procedural instructions. A smart pen cap provides step-by-step instructions for many procedures related to MDI therapy, such as the sequence of steps to properly operate an insulin pen, or a smart pen cap. These Instructions For Use (IFUs) are preferably loaded onto the smart cap system (pen cap and phone) and could be communicated to the patient by either (1) display on the Smart cap phone app or audibly to improve conformance to procedures and eliminate the need for the patient to carry or read IFUs. The IFUs and the therapeutic procedure(s), such as when to administer oral medications, insulin and other drugs and any predetermined doses, can be loaded by the patient (downloaded from the cloud) or the patient's HCP. Patient needs vary over time and as the disease progresses, and as specific IFUs and procedures become irrelevant to the patient, they can be replaced or updated as necessary. Also, as the smart injector evolves into a system that includes dose capture for oral medication, blood glucose data, and carbohydrate estimation, the relevant IFUs and procedural updates can be loaded onto the patient's device. This feature should reduce the burden to the patient, since all the relevant guidance is resident in the system and accessible in a moment's notice, but only on demand by the patient.

Embodiments of the invention preferably communicate to effect timely and automatic replenishment of the drug. This also enables the drug or device provider to send additional information to the patient. Embodiments of the invention collect the data on a personal level, and enable optionally selling data to agencies that make informed public decisions. Other features that could be included in a smart injection device for insulin therapy include: (1) transfer of patient data, such as prescription medication, automatically populate forms in advance of an office visit with PCP or other HCP, (2) emergency notification, such as call out to ER or HCP, (3) GPS, (4) location of individual, (5) alert patients when they approach restaurants where they or other patients have frequented, that is, for example, diabetes friendly businesses, (6) a lookup feature to find relevant individuals in the patient's network using the cell phone contacts, (7) ability to adjust drug release rate in response to a physiological need, (8) games, rewards, and e-coupons could be pushed to the patient, and personalized.

The elements of a smart pen preferably include several features. One is the required metrics, including insulin level in the device, delivered dose, dose confirmation, date/time of dose, and a bolus calculator.

One embodiment of the invention incorporates a finger print reader to eliminate use of the device by someone other than the intended patient.

Data captured by a smart system according to an exemplary embodiment of the invention includes glucose concentration, insulin, carbohydrates ingested, stress level, exercise, blood pressure, blood glucose low and high excursions to intelligently recognize patterns. Also, genetic traits are preferably captured in the system.

Embodiments of the invention advantageously provide the ability to identify potential failures in a manufacturing lot, or to predict a potential failure in a lot.

Embodiments of the invention provide coaching, motivating, and rewards to promote behavioral change. They provide the right information at the right time.

Embodiments of the invention include sensing technologies. These include sensors built into companion devices such as a watch, sock, or food scale to diagnose or monitor (such as temperature, moisture, glucose, heat, caloric intake, and so on). A reduction in foot temperature can be an indication of diabetes related circulation problems. Pairing a food scale and a camera phone allows for better estimation of carb content of food. Moisture or sweat detection is a marker for exercise level. Analysis may help identify electrolyte imbalance.

Implantable sensors, preferably nano sensors, monitor biological function and dispense drugs.

Continuous glucose monitoring technology is preferably placed on an insulin delivery needle for glucose detection prior to bolus or continuous delivery with a single needle stick.

Temperature sensors are imbedded in a delivery device to alert out of range warning for a drug.

In some embodiments, cooling technology is embedded in the insulin delivery device to prolong drug life.

Systems according to the invention preferably track multiple symptoms (such as migraine pattern) and multiple medications in a personalized manor. The system further preferably includes a smart phone that runs functional tests including vibrational tests for neuropathy, a 20 ft walking test for MS, using the phone camera to track eye motion for eye, neurological disorders, dizziness, a sound test for hearing loss. The cell phone can be paired with lab-on-a-chip technology for home blood analysis.

Embodiments of the present invention preferably include adherence technologies, such as an avatar (that is, a digital puppy or person) on a device that visibly gets sicker the more you miss your scheduled therapies. This aides with diabetes management to help remind patients of the effect of being out of ideal glucose ranges. For other chronic diseases such as MS or RA this could be helpful because many of the symptoms of non-adherence are not immediate.

According to an exemplary system, a device is linked to an incentive program to reward compliance or choosing healthier restaurants.

Embodiments of the present invention use capacitive or resistive sensors to identify when the injector is in contact with the skin. They use a pressure sensor in the pen needle to determine when dose delivery is complete.

An exemplary system advantageously identifies and flags patients that require intervention. Patients not requiring intervention don't need to visit the doctor as frequently, thus saving on medical expenses, and enabling a "virtual" office visit. The exemplary system enables personalized diabetes education and personalized diabetes support.

An exemplary insulin pen snaps into a smart sleeve, that is enabled with proximity detectors to identify the position of the plunger in the pen. The smart device is preferably used to facilitate titration. The data collected in a patient database is formatted and provided to the doctor in advance of an office visit. Relevant POC testing is preferably incorporated into the device.

Certain smart insulin pen caps may be able to detect different drugs. However, no known devices are used to detect changes to a drug. Embodiments of the invention determine whether insulin has been damaged. This capability enables a two part pen cap design. The sensing determines damage to the insulin earlier than the human eye and notifies the patient. The sleeve portion remains attached to the insulin pen for the entire use life of the pen. Alternately, the sleeve portion of the two part pen cap has two opposing windows that could allow the patient to inspect the insulin when open and ensure that no ambient light enters the sensing zone when closed.

Embodiments of the present invention separate a smart insulin pen cap into two elements; (1) the primary element is a sleeve that extends from the connection point on the body of the insulin pen to the shoulder surface of the pen which is in close proximity to the base of a pen needle, when attached. The secondary element in the two-piece pen cap is one of (1) a retractable "end cap", or (2) a removable "end cap" that is used to protect the delivery end of the insulin pen from contamination and/or damage. This configuration would allow capture of the exact time the dose is delivered to the patient and enable a significant number of preferred features not possible with the single piece pen caps. These include a down counting timer to confirm the proper hold time after the plunger movement has stopped to minimize or prevent leakage of injected insulin from the skin. An adjustable locking hub can be incorporated into the open end of the pen cap to allow the cap to be easily secured to insulin pens with some variation in barrel diameter.

Embodiments of the invention receive BG targets and self blood glucose monitoring data, and recommend dose changes when a non-in-target pattern is demonstrated. Embodiments of the present invention also preferably monitor the start and finish of the injection process. If the time is above or below the usual duration or if the trend is increasing or decreasing, the system contacts the user or their HCP to offer solutions.

Embodiments of the present invention include sensing to indicate whether the non-patient end of a pen needle has properly penetrated the cartridge septum. If not, the patient is alerted. Embodiments of the invention preferably include a sensor to determine if there is too much air in the cartridge. If so, then an alert is provided to the patient. The patient is preferably alerted when the selected dose has been fully delivered.

Embodiments of the present invention preferably remember dosage patterns and alert the patient if a significantly different dose is selected, or if a dose has been missed. Embodiments of the present invention also indicate if and when an insulin pen is being used beyond the recommended use period, and indicates concerns about insulin stability, exceeded recommended temperatures, formation of particles or cloudy insulin.

Embodiments of the invention provide a means to receive caloric intake data. For example in one embodiment the user takes a picture of food that is analyzed for carbohydrate content.

Embodiments of the present invention provide better monitoring of frail elderly patients either living at home or in an independent living facility. Embodiments are used as part of telehealth services, or visiting nurses or home health care. A system according to the invention is preferably combined with an activity tracker, such as a FitBit, and a BGM for improved analysis.

An exemplary insulin pen cap is redesigned to hold spare pen needles on the side or inside. The top section of the pen cap is preferably retractable.

Embodiments of the present invention include a visual indicator on pen needle hubs, such as the logo and colors of the manufacturer. A sensor reads the mark to ensure a authorized pen needle is being used.

In one embodiment the informatically enabled pen cap controls the dose amount. The patient simply speaks in to the user interface and the insulin pen cap or insulin pen automatically dials the dose. The complete system preferably includes insulin dose capture, BG level, oral medication tracking, and carbohydrate estimation, and knows the amount of insulin the patient requires and could either provide that recommendation to the patient or set the dose on the insulin pen.

In one embodiment, pen needle usage is automatically tracked by the insulin pen and the cap. A magnetic switch is set by proximity to a pen needle and reset by the cap or equivalent device by polarizing and reorienting the magnetic field or erasing it to set it to a particular state (new, used, etc.). The reading of this state of the pen needle would be incorporated into the dose reading cycle.

In another embodiment a small magnetic disk attaches to the end of the pen, and is preferably set into a recessed opening near the septum. The disk has several magnetic stripes on it that are arranged as concentric circles and are placed on the side of the disk facing away from the pen.

In another embodiment a magnet is embedded into the wall of the pen needle. When the cap is re-attached to the pen with the pen needle connected, the cap reads whether the pen needle is authorized. In yet another embodiment all pen needles are serialized.

In another embodiment the insulin pen cap burns out a fuse or wire on the pen needle to mark it as used after it reads the conductance/resistance to confirm it is an authorized pen needle.

In one embodiment a skin contact sensor is used to provide feedback to the patient. The feedback may be light or sound to signify the needle is properly deployed into the tissue, or another sensor could be used to detect leakage.

Once the plunger movement stops the device preferably counts down for the recommended number of seconds and provide a signal to the patient to indicate the dose has been delivered properly and the needle can be removed.

In another embodiment sensing is incorporated into the cap to confirm to the patient when the pen is being held perpendicular to the skin surface. This is especially important when short (4 mm) needles are used and any misalignment can result in shallow injection, possible injection into the intradermal space, or potential to develop edema.

The above and related embodiments meet unmet needs. These include identifying whether a patient primes a new pen needle and how much insulin is used for priming, identifying damage to the pen needle, determining whether the patient followed the recommended use cycle for MDI insulin injection, identifying subtle variations in these recommendations that could influence health outcomes, sensing insulin leakage, and sensing the location on the body where each dose is being administered.

Embodiments of the invention meet further unmet needs including capturing the dose at the time of delivery, recognizing reuse of the pen needle, monitoring adherence to therapy and to the recommended MDI procedure, monitoring site rotation per the FIT guidance, monitoring and directing titration for (1) once a day insulin, (2) combination drug therapy, and (3) other insulin drug therapies requiring titration.

Embodiments of the invention solve the unmet needs described above, as well as others. An exemplary embodiment of the invention comprises an informatically enabled replacement pen cap for an insulin pen. The sensing technology utilizes a single light source or emitter in combination with multiple light sensors. Alternately multiple light sources and sensors could be used. The light source can be one of a Light Emitting Diode (LED) or laser, or other source capable of providing light in the infrared A range (IR-A), that is, from 800 to 1400 nanometers (nm), and preferably from 900 to 1000 nm, d. The light from the single light source is preferably split, using a light pipe in combination with an LED, or using a beam splitter in combination with a laser, to provide a number of discrete light emissions of the same wavelength that extend axially along the inside diameter of the pen cap and extend from a point near to the connection of the cap to the pen to a point near to the top of the insulin cartridge in the pen.

A single light source advantageously eliminates errors caused in the manufacturing of LEDs, such as manufacturing variation, and the need to pair or match LEDs to the same wavelength when combined into a single system or pen cap. Multiple light sensors are placed axially opposing the line of light emission produced from the single light source. A separate compartment is provided at the top of the pen cap for the purpose of examining the area local to the pen needle, that is, to identify the presence of a pen needle or whether the pen needle has been attached properly by measurement of the gap between the bottom of the pen needle and the mating shoulder on the insulin pen. In another embodiment, the pen needle sensing compartment can be incorporated into the retractable/removable end cap of the two-piece replacement pen cap.

A preferred embodiment is a two-piece replacement pen cap, wherein the primary element is a sleeve that extends from the connection point on the body of the insulin pen to the shouldered surface of the pen which is in close proximity to the base of a pen needle, when attached.

Light is transmitted through the pen and sensed on the far side, and for each of the roughly 300 plunger positions a specific light transmission signature can be determined.

In practice, each time a dose is administered the change in plunger position can be determined by comparing the light transmission signature from the new plunger position to those captured in a look-up table that corresponds with the 300 unique signatures. Other logic and/or algorithmic analysis can also be applied, such as evaluating the last known plunger position and disregarding all previous plunger positions from consideration to eliminate the likelihood of matching the new signature with a value corresponding to an erroneous plunger position, thereby improving the reliability of the sensing system.

The secondary element in the two-piece pen cap is one of a retractable end cap, or a removable end cap that is used to protect the delivery end of the insulin pen from contamination and/or damage. The overall height of the end cap can be reduced to restrict the pen needle from remaining attached to the insulin pen, that is, an end cap of sufficiently low profile to only cover the septum and the threaded hub on the end of the insulin pen over which the pen needle attaches.

(US 2014/0188074 A1 should be referenced as prior art, and prior to filing the non-provisional application, additional investigation needs to be conducted to circumvent this prior art utilizing the benefit of the informatically enabled pen cap in the method(s) for site rotation.)

BRIEF DESCRIPTION OF THE DRAWINGS

The above and other exemplary features and advantages of certain exemplary embodiments of the present invention will become more apparent from the following description of certain exemplary embodiments thereof when taken in conjunction with the accompanying drawings, in which.

Throughout the figures, like reference numbers will be understood to refer to like elements, features and structures.

DETAILED DESCRIPTION OF EXEMPLARY EMBODIMENTS

Figure 1A:
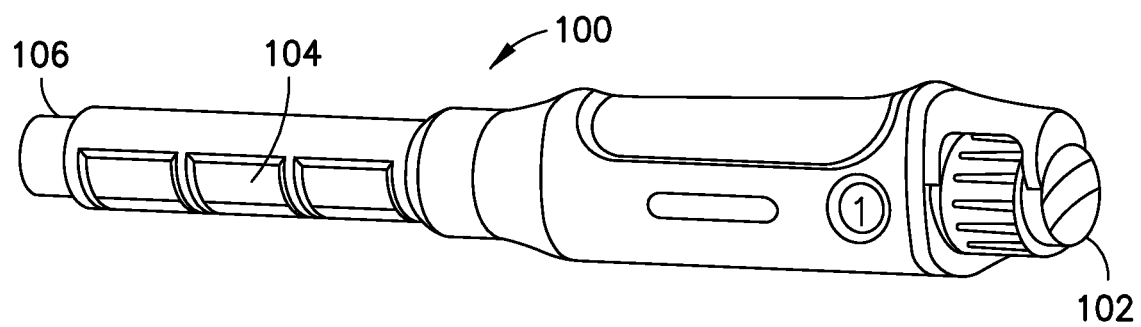
FIGS. 1A-1C illustrate an insulin pen and pen needles according to exemplary embodiments of the present invention.
Figure 1B:
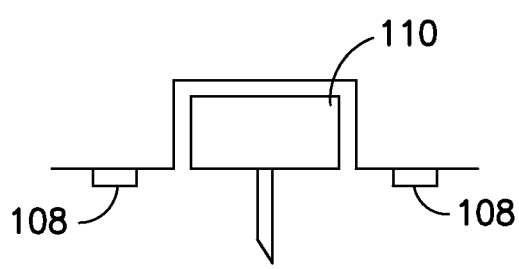
Figure 1C:
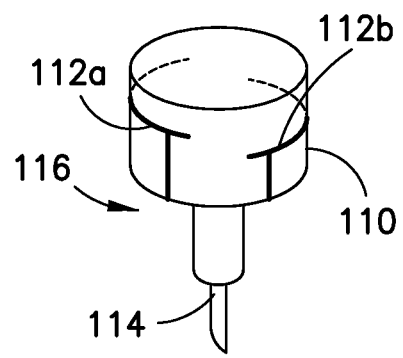

FIG. 1A illustrates a first embodiment of the invention in which an injection pen, such as an insulin pen, is modified to detect skin contact. Insulin pen 100 has a dose setting dial 102, and insulin vial 104. Insulin pen 100 also includes a distal end connector 106 adapted to receive detachable and disposable pen needles 110. FIG. 1B illustrates a cross section of a pen needle distal end having skin contact sensors 108. The contact sensors may be physical buttons that depress when pressed against a surface such as skin, or they may be proximity sensors, capacitance sensors, electrodes to detect a change of resistance between electrodes, or any other suitable means of detecting contact with a skin surface. There may be a single contact sensor 108, or multiple sensors. FIG. 1C illustrates a further embodiment, in which the sensor contacts are built into the pen needles. Pen needle 110 includes dual traces of conductive material 112a, 112b. The traces each run from needle post 114 to the hub 116 of the pen needle, and are shaped and located to make contact with electrodes inside the insulin pen device.

Figure 2:
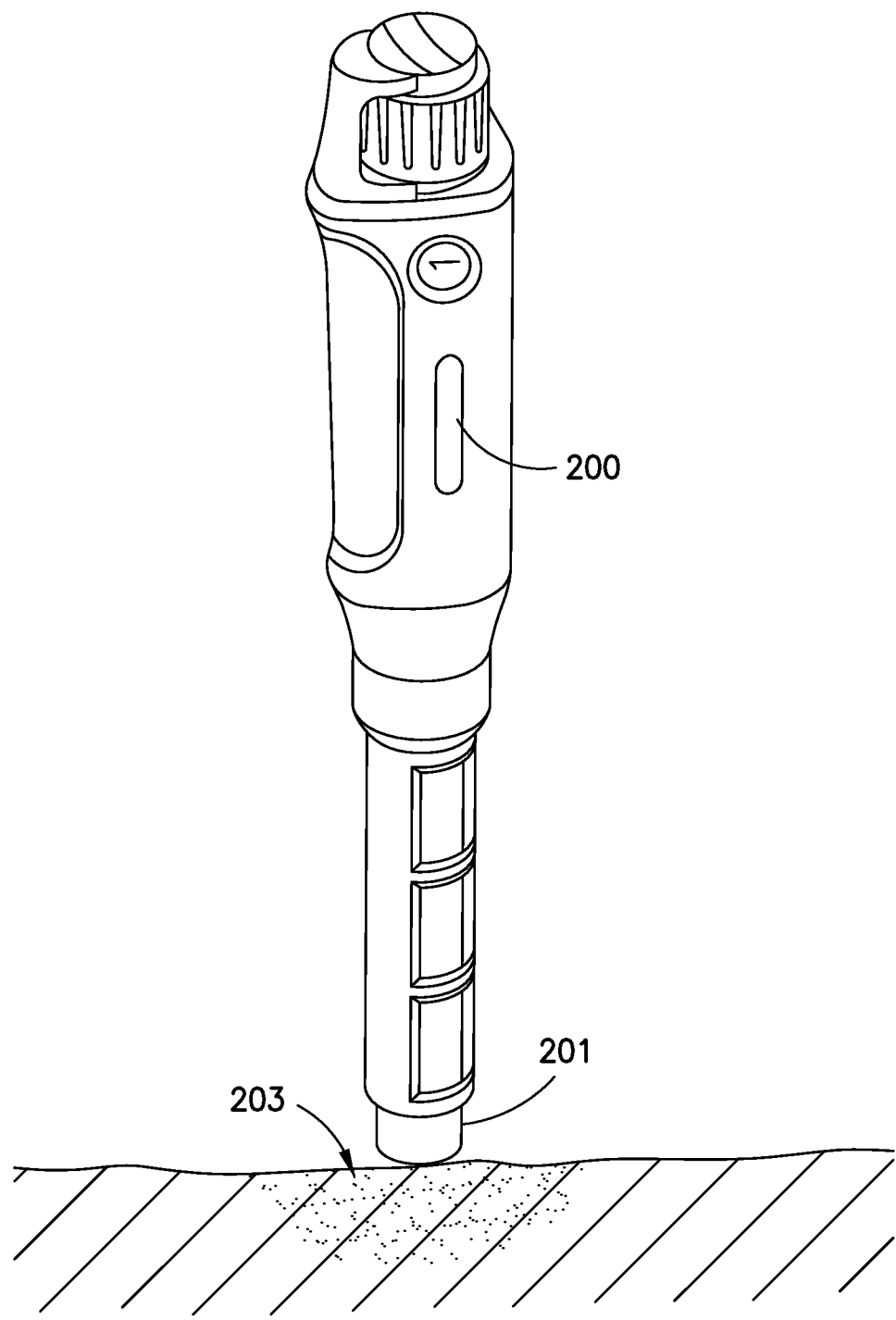
FIG. 2 illustrates an insulin pen according to another exemplary embodiment of the present invention.

In another embodiment shown in FIG. 2, an insulin pen 200 includes a sensor 201 or transducer, preferably at the distal end, adapted to detect a lypohypertrophy 203 at an injection site. The sensor 201 may utilize infrared or ultrasonic energy, or may be capacitive. Differences in skin density, color, etc. are preferably detected by the sensor. The sensor is preferably located close to the needle post of a pen needle. This embodiment preferably also tracks injection sites to assist the user with injection site rotation. The site rotation information and lypo status information detected by the device may optionally be used to delivery targeted diabetes education on a specific topic that addresses the issue detected and promotes positive behavior change.

Embodiments of the present invention preferably incorporate body mapping techniques to promote healthy injections. Body mapping techniques and systems are described in related U.S. Patent Application No. 61/911,850, filed Dec. 4, 2013, the entire contents of which are hereby incorporated by reference.

Figure 3:
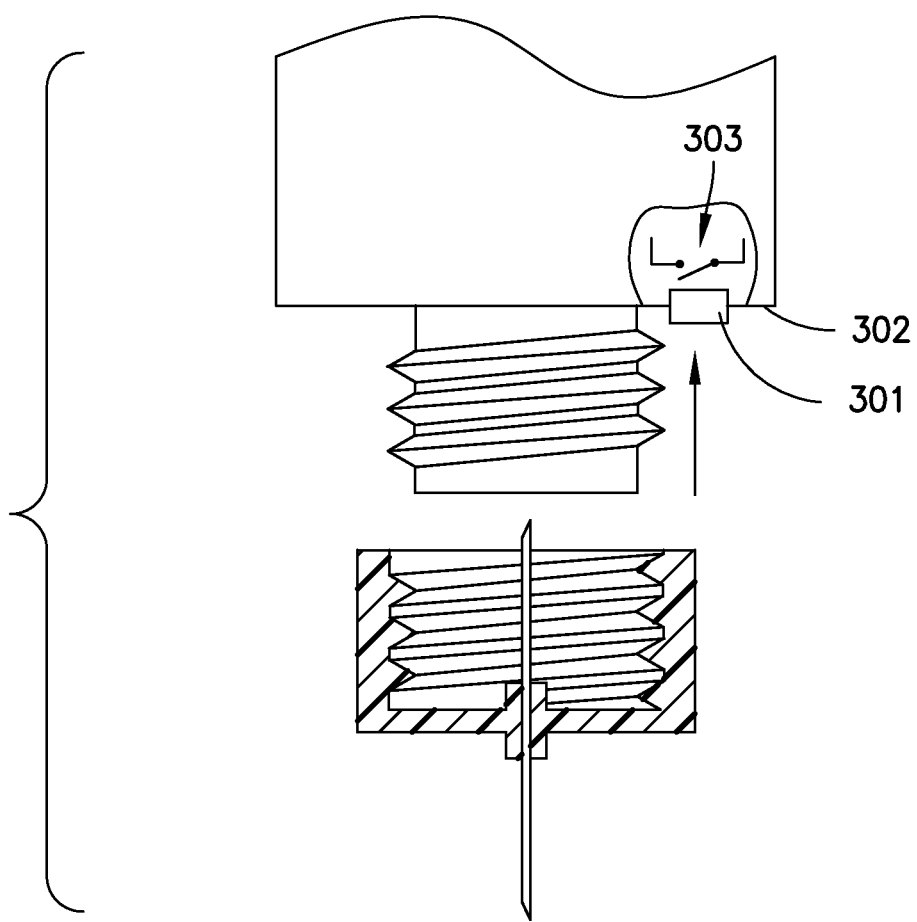
FIG. 3 illustrates an insulin pen having a pen needle detecting switch according to another exemplary embodiment of the present invention.

Conventional insulin pens include a threaded distal end that accepts a disposable pen needle. When the insulin pen is not in use, a pen needle is preferably not attached, and the distal end is covered by a pen cap. However, in some cases, a dose may accidentally be set on the device, even when a pen needle is not attached. As illustrated in FIG. 3, one embodiment of the present invention solves this problem by incorporating an interlock mechanism 301 into the distal end 302 of the insulin pen. The interlock mechanism 301 prevents insulin delivery, and preferably also prevents the setting of a dose amount until and unless a valid pen needle is attached to the insulin pen. A sensor or contact switch 303 is preferably incorporated into the distal end 302 of the insulin pen, and the sensor or contact switch detects when a pen needle is fully attached. In an alternate embodiment, a Hall effect sensor could be incorporated into either the pen needles or the insulin pen distal end, and a magnet is incorporated into the corresponding other. Such a mechanism may also advantageously be used to minimize or eliminate pen needle re-use. For example, the insulin pen could be disabled by the interlock mechanism until the used pen needle is removed and another pen needle attached. To further enhance needle re-use prevention, the insulin pen could be designed to only accept particular pen needles, and those pen needles could be destroyed or disabled automatically after use. Such disablement could be accomplished by heat, bending, or any other suitable means.

Figure 4:
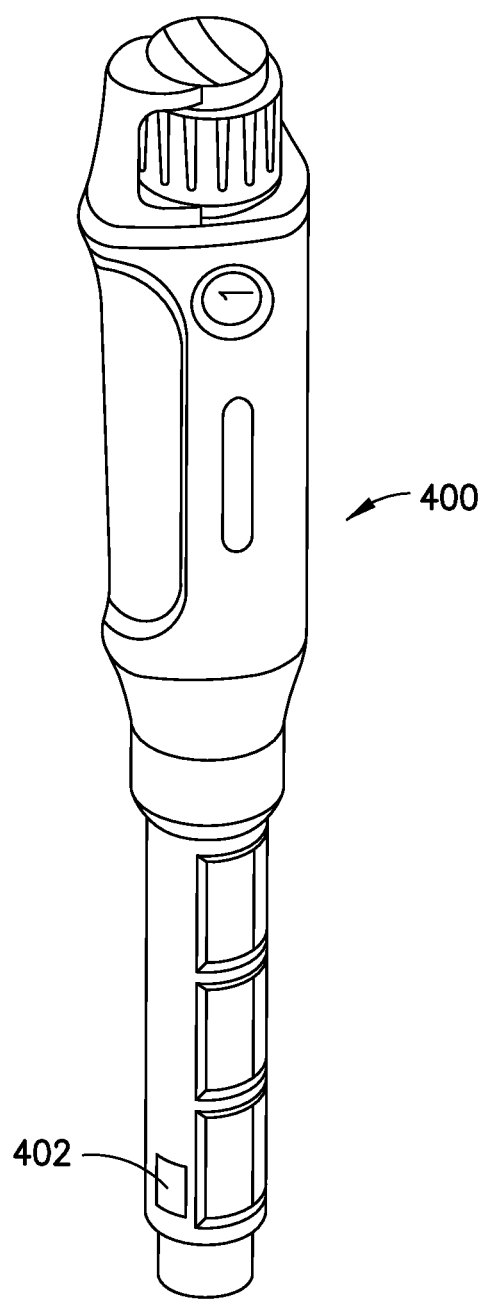
FIG. 4 illustrates an insulin pen having a fluid pressure sensor according to an exemplary embodiment of the present invention.

In another embodiment of the invention, illustrated in FIG. 4, an insulin pen 400 incorporates an in line pressure sensor 402. The pressure sensor 402, in combination with appropriate ancillary electronics, such as a processor, memory, and computer instructions, detects the pressure profile during and after a dose delivery event to ensure that residual pressure is relieved before the delivery of a full dose is complete. This arrangement has several advantages. First, occlusions and other problems may be detected by an errant pressure profile. Second, normal dose delivery events may be concluded as soon as the residual pressure is relieved, and the insulin pen may be programmed to alert the user that their dose is complete, and was successful. An in-line pressure sensor is preferred, however, a pressure sensor or transducer may also be incorporated into the plunger mechanism to indirectly detect pressure in the insulin cartridge. In another embodiment that does not require a pressure transducer, the insulin pen detects the beginning of an injection, and begins a countdown timer. The timer is set for a predetermined amount of time, such as ten (10) second, and alerts the user by visual and/or audible means when the dose time has elapsed, indicating the dose is complete. Either embodiment preferably minimizes or eliminates leakage at the injection site.

A preferred system for diabetes management includes several features as will be described below. Data capture is an important feature. Data capture includes dose amounts and time, medication verification, glucose concentration measurements, caloric intake, patient activity level, overall well being, and so on. Ideally, the data capture aspect of the system requires little or no effort from the patient. Thus, where possible, data capture is automated. The system preferably provides diabetes education on demand. This education preferably relates to, or is triggered by, data capture events. For example, if the insulin delivery system detects a lypo, this may trigger education on injection site rotation, improving the change of changing the patient's behavior for the better. In another example, insulin dose information and glucose concentration information may be analyzed to determine how often and by how far the patient strays from their target glucose range. Based on the analysis of patient dose and glucose data, the system may recommend a different insulin therapy regimen, either alone or in connection with primary care physician's review and recommendation. The system further preferably includes means for teleconferencing with a primary care physician, or other health care professionals or interested parties. The system preferably provides alerts when data indicates a problem, such as glucose concentration straying from preferred range, insulin dose not delivered per the recommended regimen, insulin supply or pen needle supply running low, or any other type of alert. The system preferably provides means for delivery information on product choices and ordering. The system preferably tracks caloric intake. In one embodiment, caloric intake data is obtained by the patient photographing food and drinks with a smart phone. Image recognition software identifies the type and amount of food and drink, and calculates the calories ingested by the patient, and also preferably records the time and date. Because the system tracks glucose concentration over time, as well as insulin doses, and caloric intake, the system can develop predictive algorithms to assist the patient in predicting the blood glucose response after a meal, and the efficacy of the insulin. The system preferably includes a bolus dose calculator. Because the system records a useful variety of data, the system can provide the user with helpful reminders, and can even provide or trigger rewards and recognition for the user based on their adherence to the PCP recommended regimen. The system is preferably linked to a social network to further encourage success.

The system described above provides several advantages over conventional systems. First, the system helps to provide a meaningful use for electronic medical records (EDRs). The system tracks adherence to a recommended diabetes regimen, and automatically flags patients who need intervention. A preferred embodiment is programmed to automatically utilize the user's smartphone to dial or otherwise alert a healthcare professional if a serious situation such as hypoglycemia is detected. Furthermore, patients who do not require intervention can minimize real world office visits, and replace them with periodic virtual office visits, further reducing medical costs, and increasing convenience for the patient. This system eliminates the need for regularly scheduled office visits, and replaces them with real time monitoring of relevant patient data such that interventions can happen right away, when they are actually needed, rather than whenever the next office visit happened to be scheduled. Healthcare professionals receive the benefit of seeing far more data, including continuous glucose data records and insulin dose data, which provides far more information to the healthcare professional.

Figure 5:
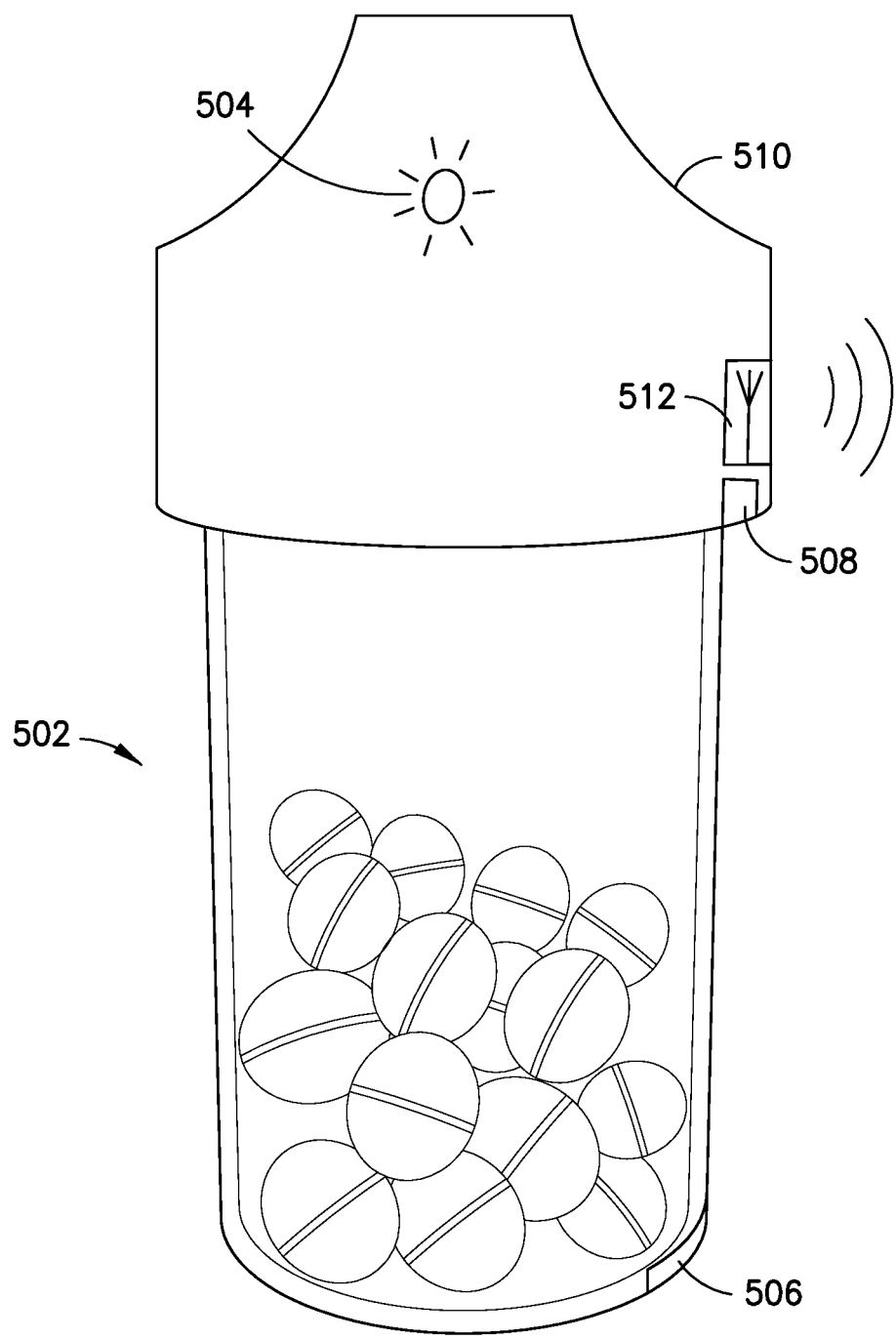
FIG. 5 illustrates a smart pill bottle according to an exemplary embodiment of the present invention.

Systems according to the present invention may also incorporate smart oral medication devices. Oral medication bottles, such as the one shown in FIG. 5, are outfitted with sensors to determine when the bottle moves, when the cap is removed, and how many pills are removed and taken by the patient. Such a smart pill bottle 502 may include visual or audible indicators 504 on the bottle or cap to alert the user whenever an oral dose is needed. The smart bottle 502 preferably includes a pressure sensor 506 to detect removal of pills by weight and a proximity sensor 508 to detect removal and replacement of the cap 510. The smart pill bottle 502 preferably communicates with the rest of the system via a wireless transceiver 512 to incorporate oral medication dose data into the overall patient database. As with insulin dose data, oral medication data may be monitored, and the patient can be rewarded for compliance with a regimen.

Figure 6:
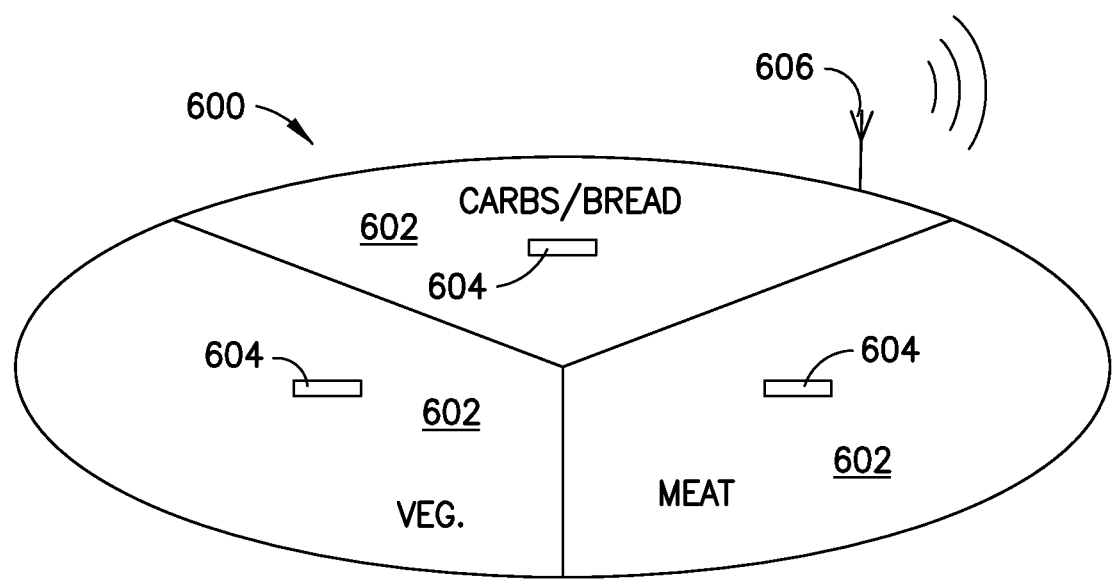
FIG. 6 illustrates a smart plate according to an exemplary embodiment of the present invention.

Another embodiment is illustrated in FIG. 6, which is a smart plate 600. The plate 600 is preferably divided into two or more sectors 602. The illustrated embodiment is divided into three sectors 602. Each sector 602 comprises a pressure sensor 604 to weigh the food placed onto that sector of the plate. Each sector 602 preferably relates to a type of food such as breads, meats, vegetables. The patient simply places the food onto the appropriate sectors of the plate, and the plate weighs the foods of various types. The pre-meal weight may be used to determine caloric intake, or the user may make a gesture indicating the meal is complete, and the smart plate can calculate the difference in weights to determine how much of each type of food was consumed by the patient, the smart plate preferably communicates with a system such as the one described above via a transceiver 606 to add caloric intake data to the overall patient database. In another embodiment a smart cup provides volume of consumed beverage data to the system. In yet another embodiment a smart scale can be used by the patient to periodically weight themselves. The smart scale similarly provides data to the overall system such that patient weight data is included in the overall patient database.

It is understood that habits take most people approximately three weeks to form. To assist in good habit forming, a system according to the present invention preferably provides alerts, reminders, and encouragement to a user. The alerts, reminders and encouragement are preferably provided via an app running on the user's cellphone. The app is preferably in communication with a cloud based patient database, and updates to reflect therapy or other changes made by the healthcare professional. Rewards can range from simple messages ("Good job!") displayed on the phone, to reward points to be redeemed in an online store, or financial rewards including discounts on further medication supplies, or reduced health insurance premiums.

Figure 7:
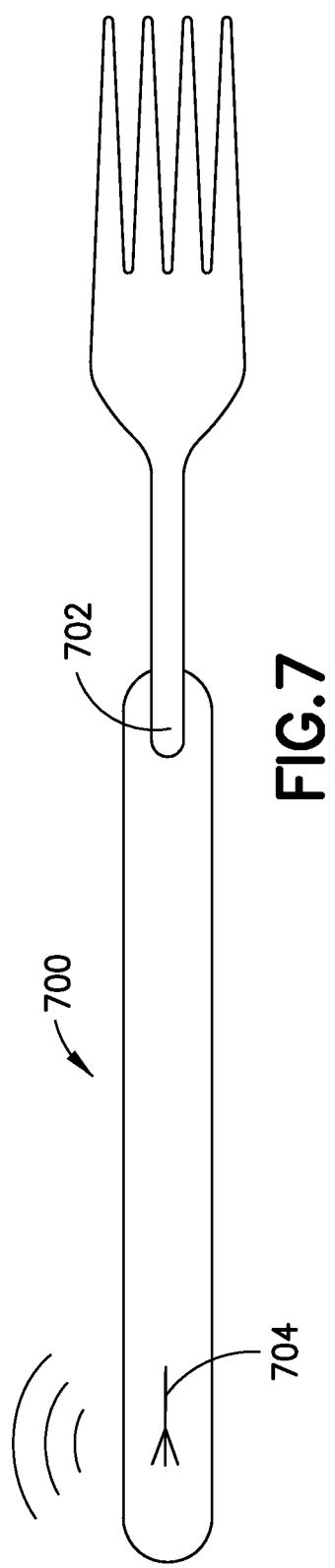
FIG. 7 illustrates a smart fork according to an exemplary embodiment of the present invention.

The smart plate described above is primarily useful for the patient's meals eaten at their home. However, it would be inconvenient for a patient to take their smart plate and smart cup out to eat. Accordingly, another embodiment of the invention is a smart fork or spoon (a smart utensil). Illustrated in FIG. 7 is a smart fork 700. The smart fork 700 is discreet and easily carried in a pocket or purse. The fork 700 analyzes the food as the patient eats, and cumulatively weighs the food eaten over the course of a meal. The smart fork preferably comprises at least a strain gauge 702 to weigh each bite of food, and may incorporate further sensors to determine the type of foods eaten during a meal, but at a minimum, the smart fork weighs each forkful and determines a cumulative food weight consumed during a meal. The smart fork 700 preferably communicates to the rest of the overall system described above, via transceiver 704 a smart phone, for example. The data is preferably transmitted to an app running on the user's cell phone, and from their uploaded to cloud storage containing the overall patient database, as described above.

In another embodiment, a smart injection system provides insulin injection functionality as described in related U.S. Patent Application No. 62/032,318, and also advantageously provides a mechanism for patients to perform self ketone testing. The system may provide a separate mechanism for drawing blood and testing for ketone levels, or the ketone testing mechanism may be incorporated into the smart injection system. In one embodiment, the overall system includes a blood glucose monitor. If the patient's blood glucose goes over 240 mg/dL, the result is transmitted to a healthcare professional. The healthcare professional then instructs the patient to perform a ketone level self-test, using their ketone tester. The results of the ketone self-test are automatically transmitted to the EMT or the HCP, depending on the results of the test.

Similarly, another exemplary device preferably tests for HbA1c, and communicates the result directly to the patient's cloud based patient database, and/or to a HCP.

Pen Adapter with Magnetic Switch

Figure 8:
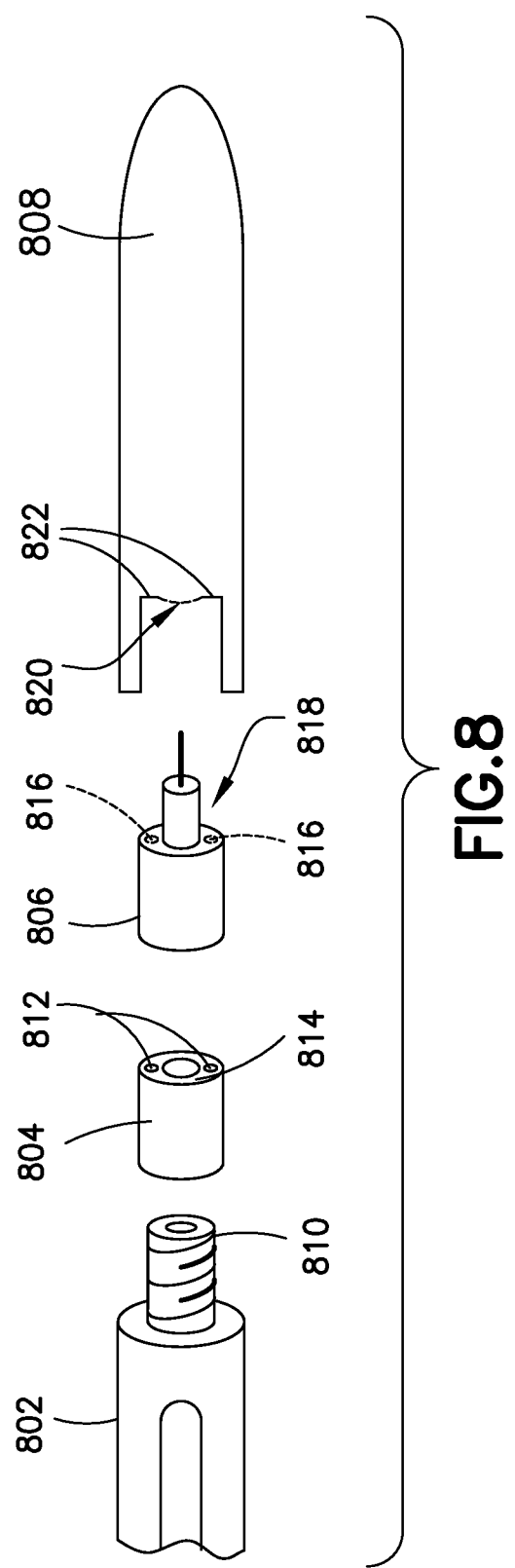
FIG. 8 illustrates an insulin pen, adapter, pen needle and cap according to an exemplary embodiment of the present invention.

Another embodiment of the present invention is illustrated in FIG. 8. This embodiments includes an insulin pen 802, an adapter 804, a pen needle 806, and a pen cap 808. As illustrated the insulin pen 802 includes a standard distal end 810 adapted to receive a pen needle. However, in this embodiment, an adapter 804 is connected to the distal end 810, and the adapter 804 in turn receives a pen needle 806. As illustrated, the adapter 804 includes at least one, and preferably multiple, magnetic switches 812. The magnetic switches are located preferably, but not necessarily, on a distally facing face 814 of the adapter 804. As further illustrated, pen needle 406 includes one, or preferably multiple magnets 816. The magnets 816 are preferably, but not necessarily, located on a distally facing face 818 of the pen needle 806. As will be appreciated, when the pen needle 406 is mounted onto the adapter 804, the magnets 816 come in proximity with the magnetic switches 812. In this manner, the adapter 804 is provided with the functionality to detect when a pen needle 806 has been attached to the adapter 804. After use, when the pen needle 806 is removed, a pen cap 808 is attached to the insulin pen 802 for storage, as is customary. The cap 808, includes a surface 820 that comes in close proximity to the distal face 814 of the adapter 804 when the cap 808 is mounted onto the insulin pen 802. The cap 808 preferably includes electronics, sensors, and settable magnets to read and optionally reset the magnetic switches 812. Utilizing this system, pen needle use and re-use can be recorded and in some cases controlled. For example, a manufacturer's pen needles could be manufactured with permanent magnets corresponding in location and orientation to a set of magnetic switches on an adapter 804. In this manner, only the manufacturer's pen needles so manufactured could be utilized together with the adapter 804. If the insulin pen includes an interlock system, as described above, then the pen could prevent use of unauthorized pen needles. Moreover, the adapter itself could include the interlock functionality in order to permit this system to work with conventional insulin pens. The system could prevent re-use by detecting if the pen needle was removed, and the adapter magnetic switches 812 reset by the cap 808. Alternately, the cap 808 could be adapted and programmed to permit re-use of pen needles, but to record each incidence of re-use, to gather data on pen needle re-use scenarios.

It should be appreciated that in the above exemplary embodiment, the magnet(s) in the cap 808 could be several small electromagnets, or the cap may simply have one large permanent magnet that "resets" the magnetic switches in the adapter 804. In either event it is preferable if the cap 808 includes electronics to detect the connection state between cap 808 and insulin pen 802, as well as detects the magnetic field(s) generated by the adapter 804 and/or the pen needle 806 as those fields interact with the cap 808. The magnets 816 in the pen needles could be incorporated into the pen needles in the hub by stickers, printing, over molding, insert molding, or any other suitable method.

It should also be appreciated that the adapter 804 could be adapted to minimize the longitudinal dimension added to the overall system by the adapter. In such an orientation the adapter 804 preferably fits over a conventional distal end of an insulin pen. That is, the inner diameter of the adapter matches the outer diameter of the insulin pen distal end. The adapter could in fact be a cylinder with openings at both ends so that the non-patient end of the pen-needle, that is the length of the insulin-pen facing needle that pierces the septum of the insulin pen and enters the insulin vial is not affected. In this version, the pen needles would not be standard size pen needles, but rather would have inner diameters that match the outer diameter of the adapter, rather than the insulin pen. In another version, the adapter is longer, and includes a distal portion with an outer diameter matching the inner diameter of standard pen needles, to permit use of standard pen needles. While screw-on connectors are standard, any suitable connection type between insulin pen and adapter, and between adapter and pen needle, should be considered to be within the scope of the invention.

While the magnets were described as being on a distal facing surface of the adapter, they could also be incorporated onto the threads of the adapter or any other surface.

In another exemplary embodiment, the magnetic switches 812 are located on the insulin pen itself, eliminating the need for an adapter 804.

Figure 9:
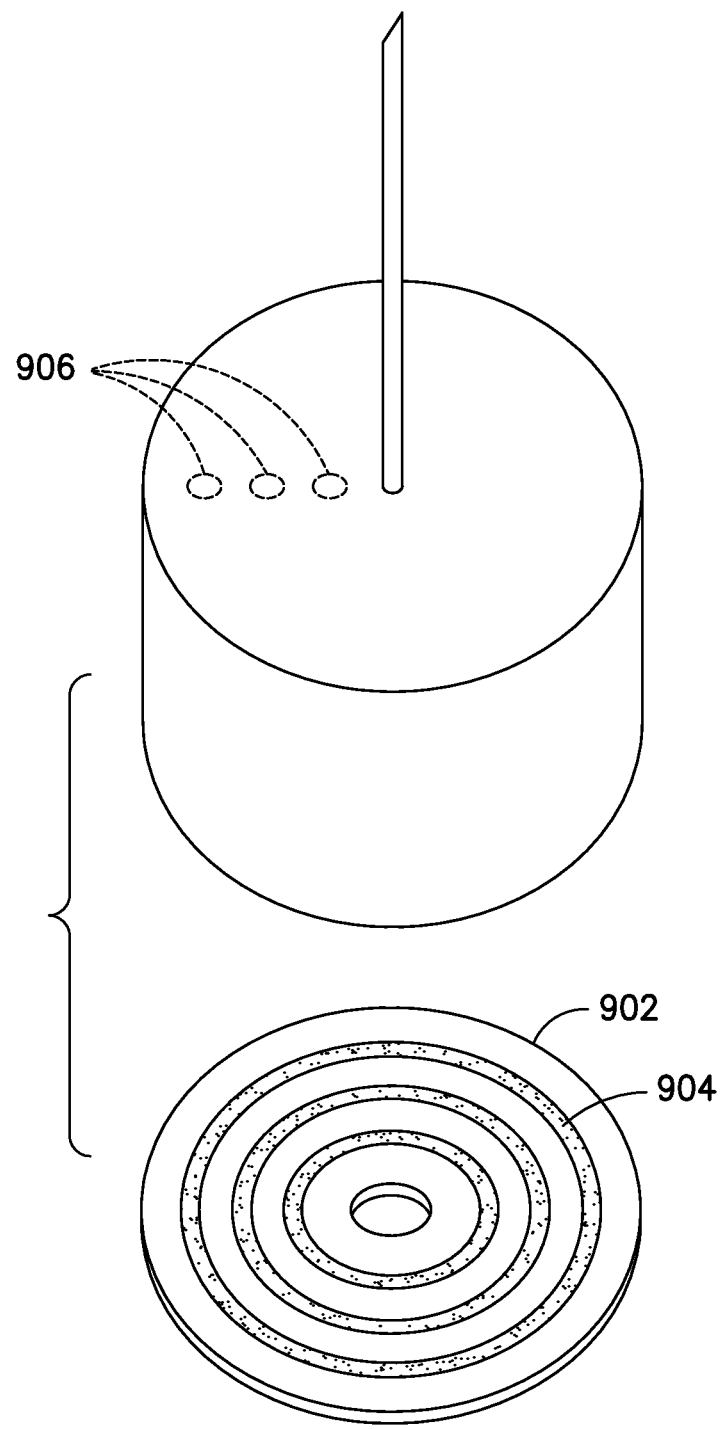
FIG. 9 illustrates a magnetically stiped disc and pen needle according to an exemplary embodiment of the present invention.

In another embodiment, illustrated in FIG. 9, a thin disc 902 is provided with multiple concentric magnetic stripes 904. The disc 902 is attached or incorporated into the insulin pen distal end, and is shaped and sized to fit within the hub of a pen needle when attached to the insulin pen. The pen needle is manufactured with multiple permanent magnets 906 located preferably on the inner surface of the hub that comes in proximity to the disc 902 when the pen needle is attached to the insulin pen. Providing the magnetic stripes 904 as concentric stripes advantageously makes the interaction between the stripes 904 and the permanent magnets 906 of the pen needle rotation independent. The stripes on the disc are advantageously encoded as the pen needle is spun down onto a threaded interface on the distal end of the insulin pen. Because the disc 902 is very thin, standard height pen needles may be used. Alternately, the pen needle hub may be made deeper, to incorporate a keyway to accept only discs from a particular manufacturer.

The disc described above could be provided one disc per disposable insulin pen, or alternately, a more robust disc could be provided for re-usable pens.

The cap 808 described above preferably reads the state of the magnetic stripes 904 on the disc 902 when the cap 808 is attached to the insulin pen. In one embodiment the disc is read by the cap when the pen needle is removed. In this manner pen needle re-use is discouraged. In another embodiment, the pen needle hub is formed with holes through the top of the hub so that the cap 808 may read the disc 902 even when the pen needle remains attached.

In one embodiment, a package of pen needles is provided, and one pen needle in the package is designated as the first pen needle for use. This pen needle has a disc 502 in the pen needle hub, and when the pen needle is attached to the insulin pen, the disc 502 is transferred from the first pen needle to the insulin pen, for use with the remaining pen needles from the package. Alternately, the device used to attach the disc 502 to the insulin pen need not be a pen needle, but could be a similarly shaped hub without a needle, provided for the sole purpose of attaching the disc 502 to the insulin pen.

In the embodiments described above, the magnetic stripes are provided on the distally facing surface of the disc 902. However, in other embodiments the magnetic feature could be provided along the outside edge of the disc, or in any other suitable location of the disc.

In another embodiment, a magnet or a plurality of magnets are provided in the wall of the pen needle. When the cap 808 is attached to the insulin pen with the pen needle attached, the cap reads the magnet or magnets provided on the pen needle wall to verify the authenticity of the pen needle. In yet another embodiment, a visual indicator is provided on each pen needle hub to indicate authenticity of the pen needle. The visual indicator may be, for example, a logo in specified logo colors of the manufacturer. The visual indicator is preferably identified by the insulin pen or cap 808.

Figure 10:
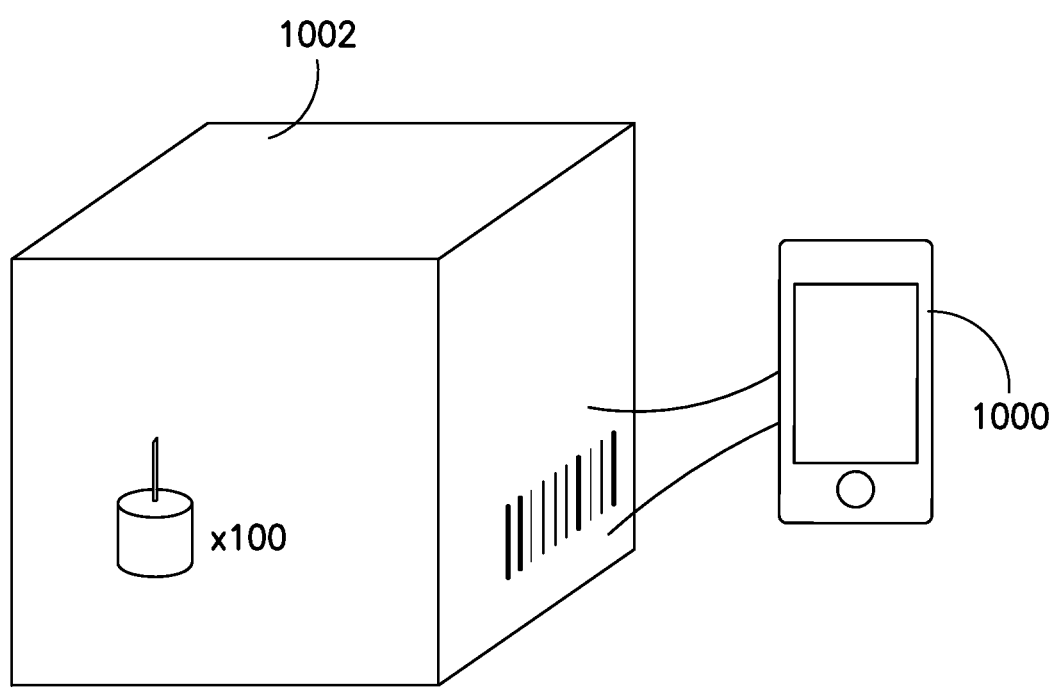
FIG. 10 illustrates a device for identifying packages of pen needles according to an exemplary embodiment of the present invention.

In another embodiment, illustrated in FIG. 10, a device 1000 is used to scan a package 1002 containing multiple pen needles. The device 1000 is preferably a handheld device such as a cell phone, or the device may also be a cap for a pen needle that includes the required electronics to perform the functions described below. Those of ordinary skill in the art will appreciate that the device performing the functions described herein need not be a handheld device or a pen needle cap, but rather could be any suitable device capable of performing the required functions. The device includes an input device such as a barcode reader, QR code reader, RFID reader, camera with optical recognition, or the like. Using any of the above input methods the device reads information on the pen needle package, such as a barcode, QR code, RFID tag, or the like, and preferably determines the package lot, model, and manufacturing information. Based on the information, the device preferably determines how many pen needles are provided in the package. Based on the number of pen needles in the package, certain features of the system may be activated for only that number of uses, in order to discourage pen needle re-use. For example, dose capture features, as described in related U.S. patent application Ser. No. 14/485,749, referenced above, may be enabled only for N number of uses, where N is the number of pen needles in the package scanned by the device. Alternately, a label or other indicator could be provided on individual pen needles, and certain features would be enabled or disabled based on the information provided in the indicator. As an example, if the pen needle is identified as from a particular manufacturer, additional features of the system are enabled. As a further example, scanning the barcode on a box of pen needles or syringes enables or restricts access to online education materials for the patient. As an example, an online coach can be provided via a website, or the like, and access to the online coach is limited to patients with a user account on the website and a valid code from a product box. Incorporating education services into the overall diabetes management system according to an embodiment of the invention advantageously provides an opportunity for risk sharing and cost reduction through combined education and smart devices. As another example, different tiers of services could be provided based on different brand and device combinations. For example, three tiers, gold silver and bronze, could be provided. As yet another example, the data recorded by the system, including doses of insulin, glucose measurements, caloric intake, exercise, and the like, could be utilized in a videogame-like interface to drive and encourage compliance with the HCP recommended regimen and an overall healthy lifestyle.

In another embodiment, a location device such as a GPS chip is incorporated into an insulin pen or smart cap for the insulin pen. The GPS location data advantageously can assist with lost insulin pens, lost smart caps, and even lost people, in the case of a hypo or hyperglycemic patient who loses consciousness.

Figure 11:
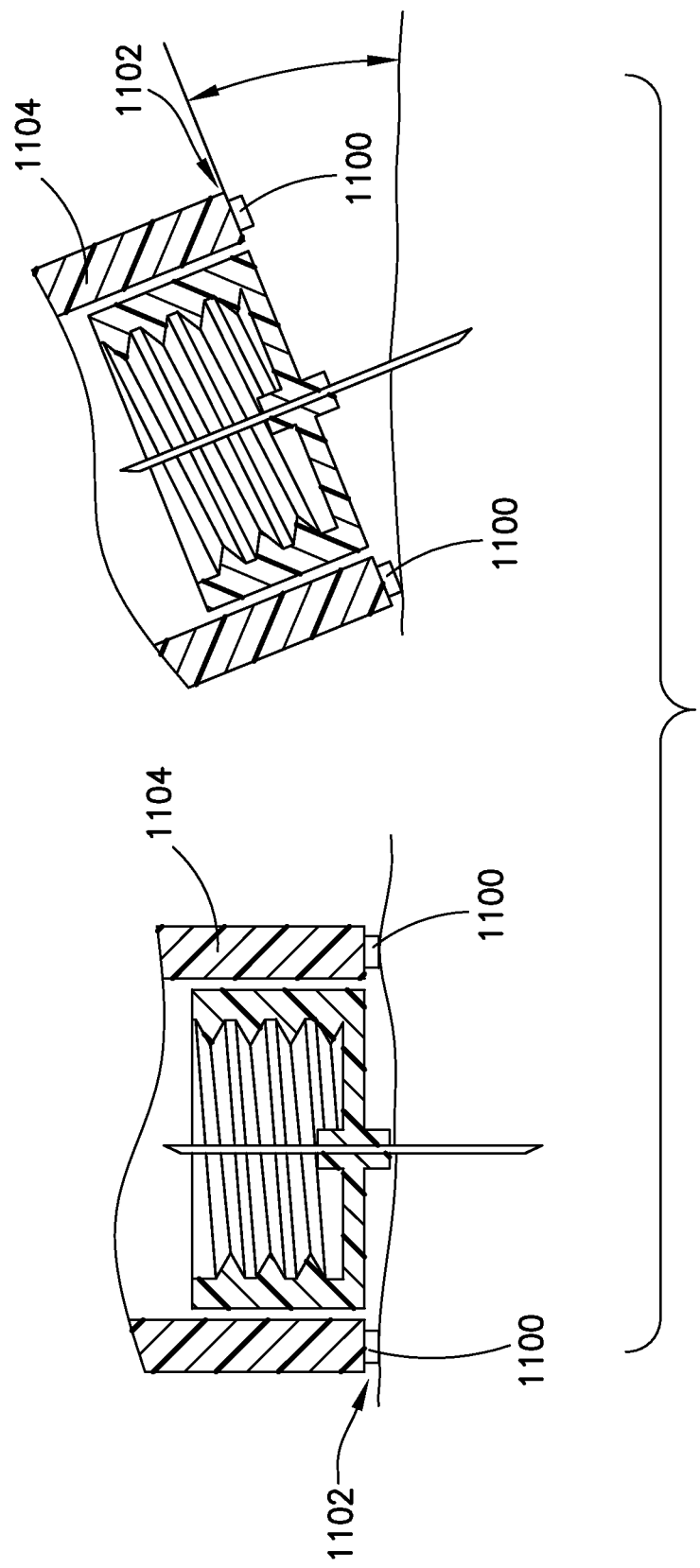
FIG. 11 illustrates an insulin pen having skin contact sensors according to an exemplary embodiment of the present invention.

Typical insulin pen needles extend only 4 mm. Accordingly, it is important that the insulin injection be made at close to 90 degrees relative to the skin. Any significant departure can significantly reduce the effective length of the needle, and the penetration depth thereof, resulting in an injection that is too shallow, and potential formation of edema. An embodiment of the invention includes a sensor or level that verifies the injection is made within acceptable tolerance of 90 degrees from the skin surface. As illustrated in FIG. 11, such sensor may be contact sensors 1100 on the distal face 1102 of the insulin pen 1104 surrounding the pen needle. Preferably multiple sensors on opposite sides of the needle would be used, and all of the sensors would need to detect contact to verify a 90 degree angle relative to the skin surface. Alternately, any other sensor or level detecting technology could be used. Examples include an optical emitter and detector on the distal face of the insulin pen. Reflection will be maximum at a 90 degree angle, and so the level of reflected light in such a system corresponds to the angle of the insulin pen relative to the skin surface.

In another embodiment of the invention, an insulin pen, a smart cap as described above, and access to educational materials related to diabetes and insulin therapy, and the like, are provided in a starter kit to new patients beginning basal therapy. The smart cap and related devices in the system transmit dose and other information to the patient database, for remote monitoring of the patient to assist with initial titration, and to keep the HCP aware of the patient's progress with their new therapy.

Figure 12:
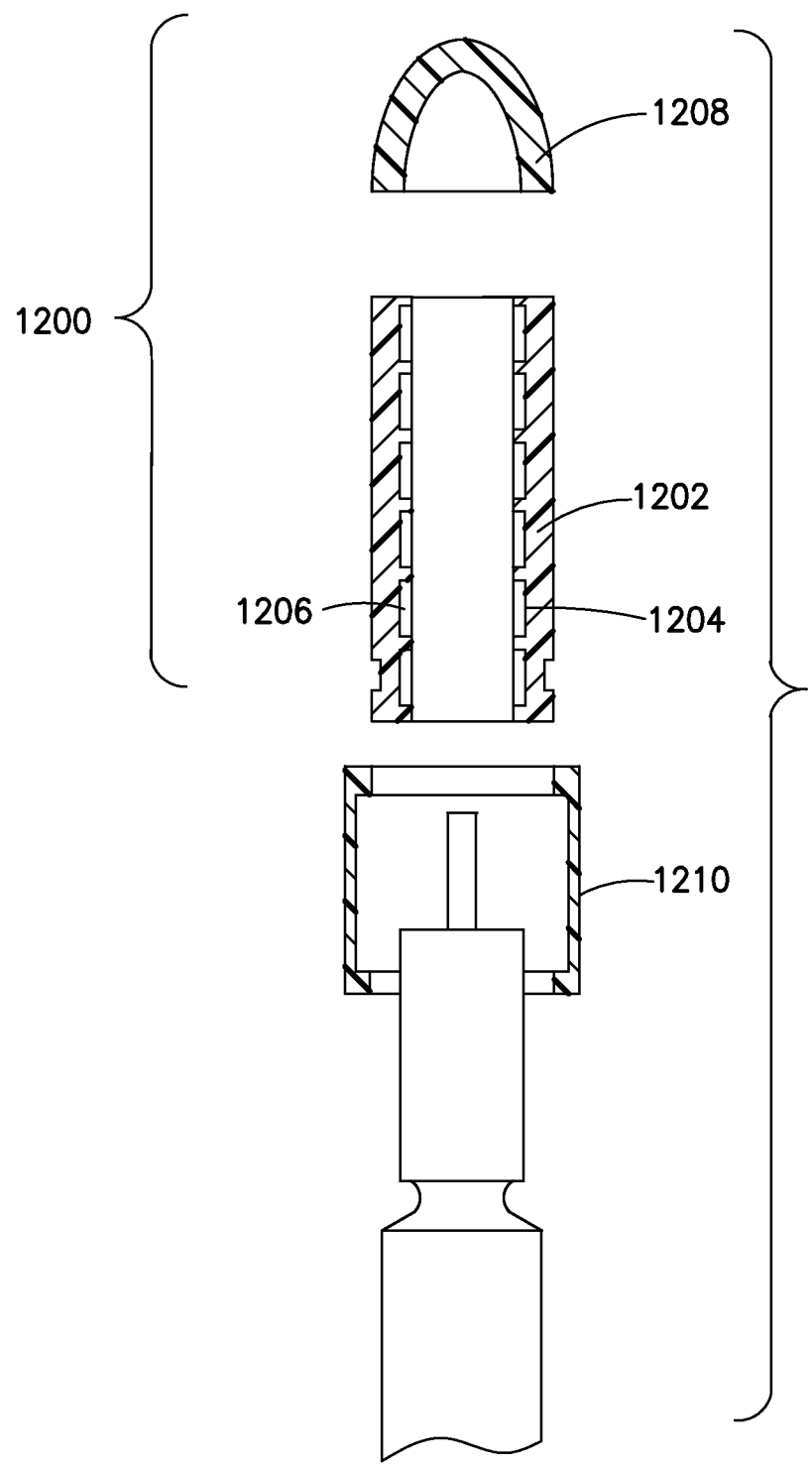
FIG. 12 illustrates a two-part smart insulin cap according to an exemplary embodiment of the present invention.

Another embodiment of the invention shown in FIG. 12 is a smart cap 1200 such as the one described in U.S. Pat. No. 8,817,258 and WO 2013/177135, but modified. In the modified embodiment, the smart cap 1200 is provided in two parts. The first part 1202 is a sleeve that includes the emitters 1204, sensors 1206, and other mechanisms described above and in the related incorporated documents. The second part 1208 is a smaller detachable or retractable portion that is removable or movable to expose the distal end of the insulin pen and pen needle for injections. The second part 1208 may be detachable, in which case it is preferably of extremely low cost, since none of the sensing technologies are incorporated. Alternately, the second part 1208 may be retractable or hinged, and stay connected to the first part. The first sleeve part 1202 may be permanently affixed to the insulin pen, or may be locked onto the pen, such as in the case of a smart cap device added to a standard insulin pen, with a locking hub 1210. In this embodiment, since the sensing technologies of the smart cap remain on the pen between injections, dose delivery can be confirmed in much greater detail. For example, a skin contact sensor can detect when the insulin pen has contacted the skin, the emitter bank and sensor bank combination can detect movement of the plunger, the plunger stopping, and the once the plunger stops the device can count a predetermined period of time to allow the insulin to be fully absorbed into the skin. The device can alert the patient with audible and/or visual alerts that the dose was successfully delivered, and record the time and amount of the dose in the overall patient database.

In another embodiment of the invention the insulin pen or the smart cap are provided with a microphone and dose amount actuator. The processor is programmed for speech recognition. The user simply speaks the dose amount and the insulin pen or the smart cap automatically dials the requested dose using the dose amount actuator.

In another embodiment of the present invention, pen needles are provided with a conductive strip. The conductive strip may be painted, printed, or etched onto the pen needle. Of course these methods are merely exemplary, and any other suitable means of providing a conductive strip onto the pen needle may be used. The conductive strip is preferably cut when inserted or removed from the insulin pen, providing an open circuit that is detectable by the insulin pen or a related device, such as an adapter fitted between a standard insulin pen and the pen needle with conductive strip. In this manner, used pen needles may easily be identified. Based on the state of the conductive strip, features of the system are enabled or disabled, including but not limited to dose capture features as described in related U.S. patent application Ser. No. 14/485,749, and including preventing dose delivery if a used state of the inserted pen needle is detected.

In another embodiment of the present invention, pen needles are serialized during manufacture. The serial number is preferably painted, printed, etched, magnetically encoded on a thin film provided on a bar code, QR code, RFID tag, or the like, onto each pen needle. Of course the methods described above are merely exemplary, and any suitable method of providing a serialized number and related information onto a pen needle could be used. A reader device is provided to read the serialized information provided on each pen needle. The reader device is preferably incorporated into an insulin pen cap, so that the pen needle may be conveniently read each time the cap is replaced onto the insulin pen. The information is preferably, but no necessarily, encrypted. The information preferably identifies authentic or genuine pen needles provided by a particular manufacturer. Providing serialized information provides the system with additional capabilities to track or minimize re-use of pen needles, and to prevent or minimize use of pen needles provided by a different manufacturer. As described above, certain features of the system, including dose capture features, can be enabled or distabled based on the serialized information read by the reader device. For example, in one method of use, the reader device is provided in the insulin pen cap. After injecting a dose, the user replaces the insulin pen cap with the pen needle still attached. If the reader device in the cap detects an authentic unused pen needle, the dose information is transmitted to a patient database. If, however, the reader device detects an inauthentic pen needle, or a re-use of the pen needle, the dose information is not transmitted to the patient database.

In yet another embodiment, the insulin pen cap is modified to assist with attaching pen needles to the insulin pen. In this manner, the insulin pen cap, including a reader device, determines whether the pen needle is authentic and unused when the pen needle is attached to the insulin pen. In this embodiment, all or a subset of features may be enabled or disabled based on the information read from the pen needle by the reader device in the cap. Advantageously, because the cap is incorporated into the process of attaching the pen needle to the insulin pen, dose delivery may be prevented unless and until authentic, unused pen needle is attached to the insulin pen.

In another embodiment, the pen needles are provided with a fusable circuit. The fusable circuit is preferably of a designated value, the value preferably resistance or conductance, although any other suitable physical property such as inductance or capacitance could also be used. A reader device is provided, preferably in the insulin pen cap. The reader device measures the physical property to determine if the pen needle is authentic and unused. If the pen needle is unused, then after use, the cap preferably delivers a current to the pen needle to cause a one-time change in the circuit, such as clearing a fuse or open circuiting a thin wire. In this manner the pen needle is marked as having been used. As with the embodiments described above, a subset or all features of the system may be enabled or disabled based on the state of the fusable circuit of the pen needle.

In another embodiment, an insulin pen is provided with one or more LED's or other visual indicators. In an exemplary embodiment, the LED's provide an indication to the user of the states of the pen needle attached to the insulin pen. For example, a "green" indicator may indicate an authentic, unused pen needle. A "red" indicator may indicate an authentic, but used, pen needle, and a "yellow" indicator may indicate an inauthentic pen needle. Three different LED's may be used, one for each of the colors red, green and yellow, or a single multi-color LED may be provided. Alternately, different visual displays such as liquid crystal may be provided. Audible indicators may be provided in addition to or in lieu of visual indicators. For example a beep pattern may indicate the status of the pen needle. A vibration motor may be provided in the insulin pen or the cap, and the vibration can be used to indicate the status of the pen needle.

In another embodiment, a pen needle remover device is incorporated into an insulin pen cap. Such a removal device is described for example, in U.S. Pat. No. 8,829,394 to Limaye, the entire contents of which are hereby incorporated by reference.

In yet another embodiment a small MEMS device is provided on the pen needle. The MEMS device may be a simple switch, that is settable and readable by the reader device. Alternately, the MEMS device may be a flow sensor used to determine the dose delivered through the pen needle. A MEMS flow sensor that is already detecting and measuring a dose amount delivered advantageously may also be used to indicate that a pen needle has been used.

A thermal time of flight (TOF) sensor according to an exemplary embodiment of the present invention will now be described. The sensing element for the thermal TOF sensor is preferably fabricated on a silicon die in a Micro Electro-Mechanical System (MEMS) wafer scale manufacturing process. The sensing element is comprised of three separate parallel traces on the surface of the MEMS chip, which connect to three thermistors. The central trace is a heating element, and the two outermost traces are sensors. The MEMS manufacturing process is extremely accurate and capable of producing these traces to very tight tolerances and exacting proximity to the target location. The sensor is combined into an assembly that includes a fluidic path, an EEPROM and electrical connections for power and data transfer. In operation, the three traces are exposed to the fluidic path and when the heating element is energized a small amount of energy is imparted to the fluid. Depending on the direction of fluidic flow, one of the sensors adjacent to the heating element will measure an increase in temperature above the previous ambient condition, enabling the flow rate to be calculated. This technology is advantageous because of the reduced size of the MEMS sensor, but unfortunately, the cost of MEMS TOF sensor assemblies, even in high annual usage, can be cost prohibitive for most single use or disposable medical device applications, such as a disposable insulin pen or pen needle.

To enable the use of MEMS TOF sensing for disposable medical devices an interface is required between the sensor and the fluidic path. The requirements of this interface include: (1) a number of conductors embedded within a membrane or insulated element, (2) the conductors in the interface would be of the same relative size as the conductors/traces on the MEMS TOF sensor, (3) the conductors in the interface would be placed in the same relative proximity as the conductors/traces on the MEMS TOF sensor, (4) ideally, the conductors and the local area of the interface would be able to flex when placed in contact with the traces on the MEMS TOF sensor to allow for manufacturing and assembly tolerances, and (5) the conductors would provide near zero loss of signal, that is, heat transfer, or delay in signal transfer. Alternate embodiments of this invention providing further advantages for insulin injection include the following; (1) since the flow of insulin during an injection occurs in only one direction, the interface only requires two conductors, one for the heating element and the other for the downstream sensor. (2) The size and shape, primarily the length in direction of flow of the two contacts on both the MEMS chip and interface can be optimized to provide for a robust tolerancing scheme, thereby enabling correct alignment when the sensor is placed in contact with the interface.

Systems and methods according to exemplary embodiments of the present invention advantageously assist users in complying with their diabetes care regimen as prescribed by their healthcare professional (HCP). For example, in connection with a dose capture system as described in related U.S. application Ser. No. 14/485,749, an exemplary system can help a user maintain their target blood glucose concentration and help to recommend adjustments in dose amounts. In such a system the user or their HCP enters blood glucose targets which are stored by the system. The user then takes periodic or continuous blood glucose readings. Blood glucose readings are entered into the system and stored, either by the user, or automatically by the BGM. Stored blood glucose measurements are analyzed by the system and compared to the blood glucose targets, and if a pattern of deviations are recognized, an alert can be provided. Moreover, either automatically or in connection with a review and recommendation by a HCP, changes in insulin dose amounts can be made to promote healthy blood glucose levels and better control for the user.

Another source of problems with blood glucose control is the efficacy of the insulin injection. Users are typically instructed to keep an insulin pen in place during an injection for approximately 10 seconds. This is to provide time for the insulin dose to be fully injected, and to dissipate into the skin of the user. Early withdrawal of the pen needle can cause leakage or weeping of insulin from the injection location, thus reducing the amount of insulin received. An insulin pen or other insulin delivery device according to an exemplary embodiment of the invention includes a mechanism to record the duration of an injection event. For example, an insulin pen is provided with a skin contact sensor. The device can record and store the time that the device remains in contact with the skin following activation of the injection. If the durations of recorded injections begins to deviate from the recommended duration, either too short or too long, the device can alert the user, and also provide the alert to the overall patient database for review by the HCP or other interested parties. In one exemplary embodiment the device is provided with means to provide guidance to the user to offer a solution to the injection duration problem. Such information may be delivered via the user's cell phone, for example.

Figure 13:
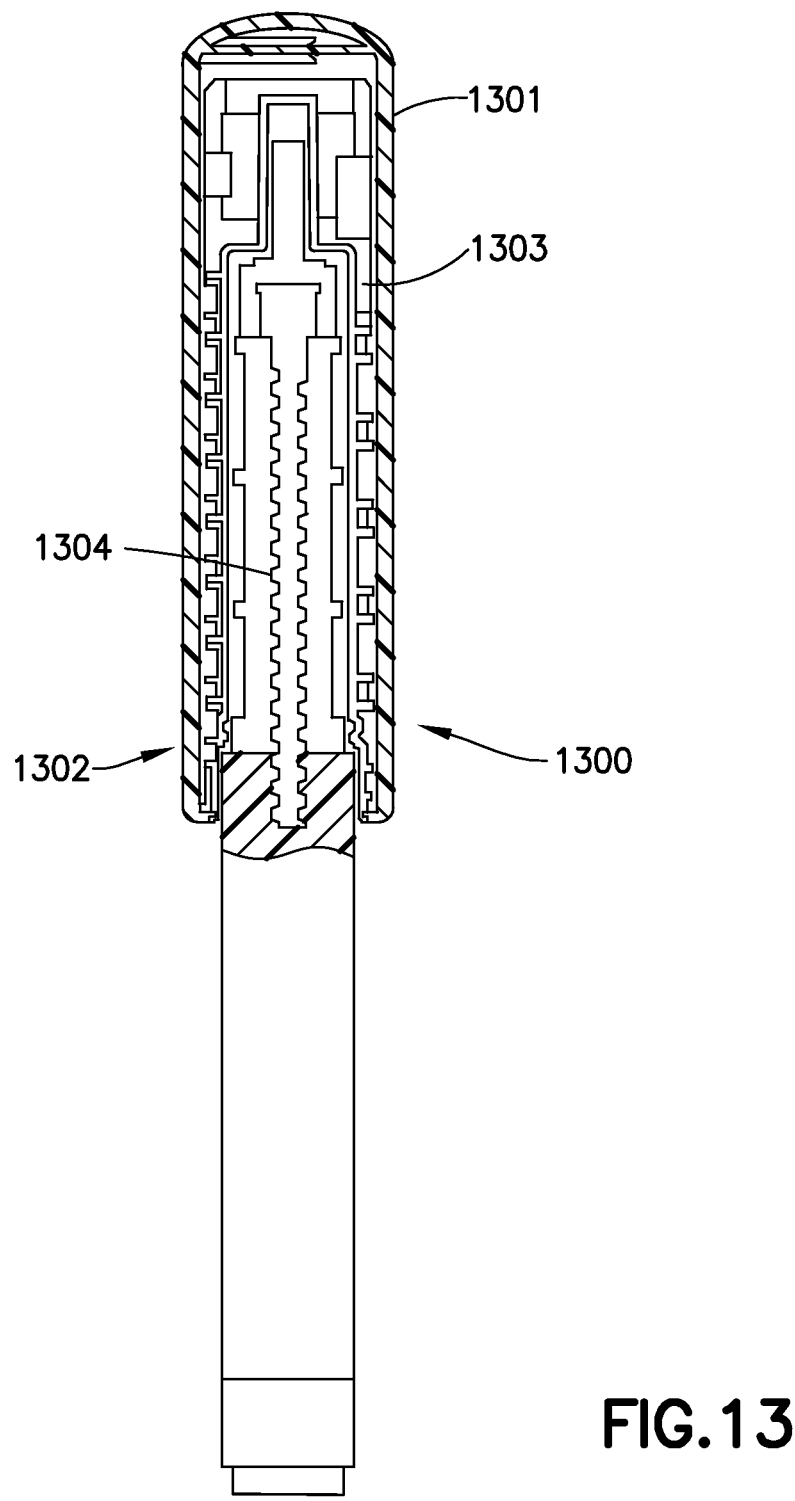
FIG. 13 illustrates an insulin pen according to another exemplary embodiment of the present invention.

FIG. 13 illustrates an insulin pen 1300 having a sensor cap 1301. The sensor cap 1301 includes an emitter bank 1302 comprising at least one light emitter, and a sensor bank 1303 comprising at least one light sensor. One such pen cap is described in detail in International Patent Application No. WO 2013/177135, and in U.S. Pat. No. 8,817,258, the entire contents of both of which are hereby incorporated by reference. As shown in FIG. 13 the emitter bank 1301 and sensor bank 1302 are oriented on opposite sides of an insulin vial 1304. In this manner, the sensor bank 1303 receives a pattern of light from the emitter bank 1302 that corresponds to a number of factors, including the plunger position, the clarity of the insulin in the vial, and air bubbles in the vial 1304. The insulin pen 1300 also preferably includes a sensor to determine when the injection is activated, that is, when the thumb button is pressed to begin an injection. Furthermore, the insulin pen preferably includes a sensor that verifies of the non-patient end of a pen needle fully penetrates the septum and enters the insulin vial. If the sensor does not sense full penetration into the insulin vial, an alert is provided to the user. If too much air is sensed in the insulin vial, either by the sensor bank, or otherwise, an alert is provided to the user. The insulin pen also preferably comprises a timing mechanism that times the injection duration and provides a visual and/or audible indicator to the user when the full duration of the injection has been reaches. Such duration is preferably in the range of 5-10 seconds. In embodiments that record the dose amount delivered to the user, the dosage pattern may be recorded and analyzed. If a significantly different dose is set by the user, or if a dose is missed, a warning is preferably provided to the user.

It is well understood that insulin becomes less effective over time, such that the user may need more of the insulin to have the same effect. This is because over time the insulin molecules are damaged. Such damage is happens more rapidly if the insulin is exposed to elevated temperatures. An insulin pen according to a preferred embodiment preferably records when a new insulin vial is inserted into the pen. Accordingly, the insulin pen can alert the user if the insulin becomes aged beyond a recommended duration. The insulin pen preferably includes a temperature sensor. If the pen experiences elevated temperatures for a duration that could affect the stability of insulin molecules in the insulin vial, the user is alerted. Finally, the emitter bank and sensor bank can advantageously detect changes in the insulin molecules inside the insulin vial by detecting a change in the light signature received at the emitter bank. Such detection is advantageously possible before the human eye can detect cloudy insulin. Accordingly, an insulin pen having an emitter bank and sensor bank preferably alerts the user to a change in the state of the insulin molecules as detected by the light signature received at the sensor bank of light transmitted through the insulin from the emitter bank. The emitter/sensor banks also preferably detect the type of insulin. Advantageously, such emitters/sensors eliminate or reduce the need for windows in the insulin pen and visual inspection of the insulin by the user.

Figure 14:
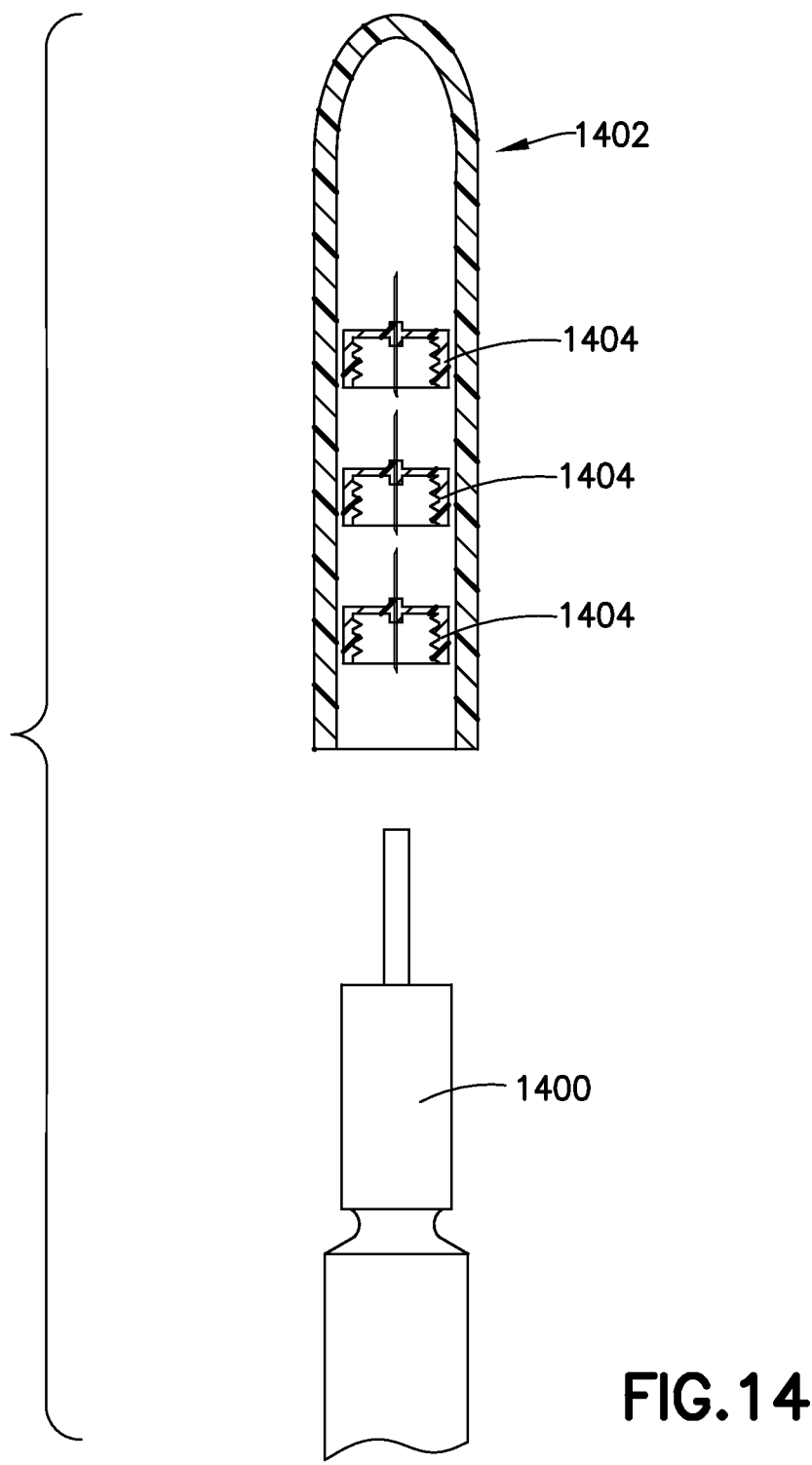
FIG. 14 illustrates an insulin pen cap with storage for spare pen needles according to an exemplary embodiment of the present invention.

One reason users re-use pen needles is because it is inconvenient to carry spare pen needles in addition to the insulin pen. In addition some users prefer to be as discreet as possible with their insulin pens, and do not want to change pen needles in public. One embodiment of the present invention illustrated in FIG. 14 comprises an insulin pen 1400, and insulin cap 1402, and one or more spare pen needles 1404 stored in a space within the cap 1402. Alternately, the spare pen needles 1404 may be stored on the side of the cap 1402. Since the insulin pen 1400 and cap 1402 are carried by the user already, the cap 1402 including spare pen needles 1404 makes it much more convenient for the user to change pen needles for each use. The cap 1402 is preferably formed to hold a spare pen needle 1404 in position for connection to the insulin pen. The cap 1402 preferably holds the pen needle 1404 with a friction fit that is snug enough to avoid the pen needle 1404 becoming dislodged while being carried by the user in a purse or pocket, but so that it is relatively easily disconnected from the cap 1402 once attached to the insulin pen. In this way, changing the pen needle 1404 remains discreet since the user merely manipulates the insulin pen 1400 and cap 1402.

Figure 15B:
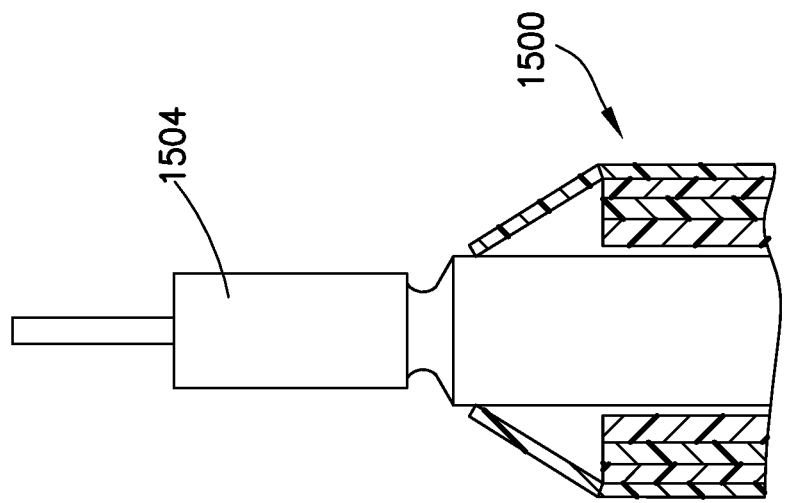
FIGS. 15A and 15B illustrate a retractable insulin pen cap according to an exemplary embodiment of the present invention.
Figure 15A:
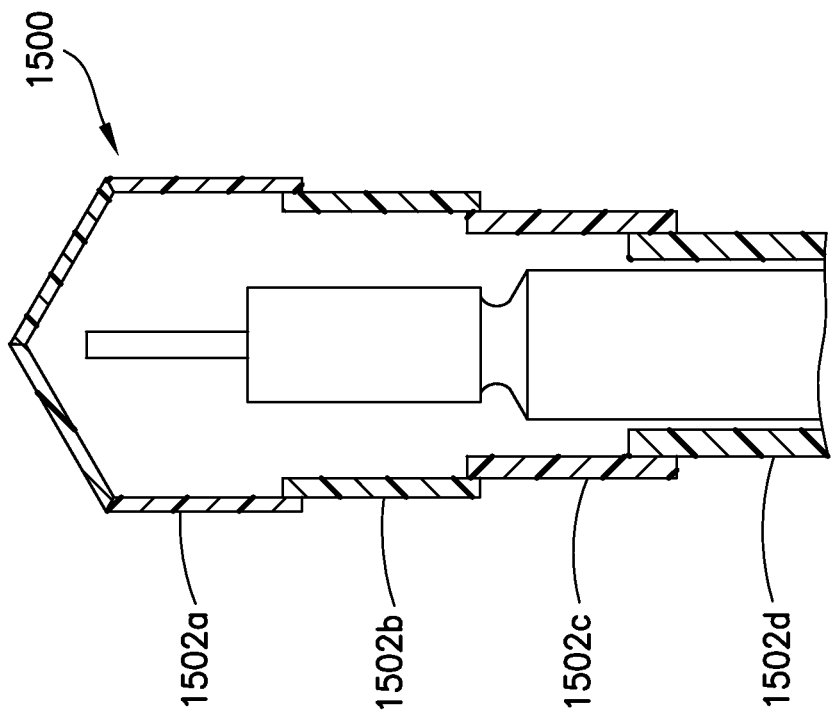

One problem with detachable insulin pen caps is that users may misplace or lose them. If electronics and communication circuits as described above are included in the pen cap, this problem becomes more severe due to the loss of a more expensive component that needs to be replaced. Accordingly, one exemplary embodiment of the invention shown in FIGS. 15A and 15B provides a cap 1500 that is permanently attached to the insulin pen 1504. The cap 1500 is preferably formed in segments 1502a-1502d so that it is retractable to expose the distal end of the insulin pen 1504 and pen needle attachment. FIG. 15A illustrates the cap in extended configuration and FIG. 15B illustrates the cap in retracted configuration. Alternately, the cap is retractable but still may be removed, such as by a snap fitting to the insulin pen, if the user desires.

Although only a few embodiments of the present invention have been described, the present invention is not limited to the described embodiment. Instead, it will be appreciated by those skilled in the art that changes may be made to these embodiments without departing from the principles and spirit of the invention.

What is claimed is:

1. A device for measuring delivered dose information comprising:
    an insulin delivery device having a proximal end and a distal end, a plunger and an insulin vial comprising insulin distal of said plunger;
    a two-part pen cap, comprising:
    a sleeve enclosing the insulin delivery device, lockable onto the insulin delivery device and comprising at least one light emitter and a plurality of light sensors, wherein the at least one light emitter is oriented to project light through insulin in the insulin vial to the light sensors;
    a second portion attaching to the sleeve and enclosing the distal end of the insulin delivery device; and
    a locking hub for locking the sleeve to the insulin delivery device;
    wherein the second portion is adapted to reveal the distal end of the insulin delivery device while the first sleeve remains on the insulin delivery device during an injection;
    wherein the at least one light emitter is positioned on the sleeve to project light through insulin in the insulin vial during the injection and the plurality of light sensors are positioned to receive light projected through insulin in the insulin vial to measure a dose delivered during the injection; and
    wherein the sleeve is programmed to detect when the plunger stops and to provide a signal indicating a successful dose after a predetermined period elapses after the plunger stops during which a skin detector detects contact of the insulin delivery device with skin.

2. The device of claim 1, wherein the second portion is detachably connected to the sleeve.

3. The device of claim 1, wherein the second portion is permanently connected to the sleeve and hinged to move from a first configuration in which the distal end of the insulin delivery device is enclosed to a second configuration in which the distal end of the insulin delivery device is exposed.

* * * * *